US011744466B2

(12) United States Patent
Hauger et al.

(10) Patent No.: US 11,744,466 B2
(45) Date of Patent: Sep. 5, 2023

(54) METHOD AND APPARATUS FOR LOCALIZING BRAIN TISSUE REGIONS CONNECTED WITH A BRAIN FUNCTION (71) Applicant: Carl Zeiss Meditec AG, Jena (DE)

(72) Inventors: Christoph Hauger, Aalen (DE); Gerald Panitz, Bopfingen (DE); Roland Guckler, Ulm (DE)

(73) Assignee: Carl Zeiss Meditec AG, Jena (DE)

(*) Notice: Subject to any disclaimer, the term of this patent is extended or adjusted under 35 U.S.C. 154(b) by 299 days.

(21) Appl. No.: 17/025,905

(22) Filed: Sep. 18, 2020

(65) Prior Publication Data

US 2021/0085182 A1 Mar. 25, 2021

(30) Foreign Application Priority Data

Sep. 20, 2019 (DE) ..................... 10 2019 125 407.8

(51) Int. Cl.
*A61B 5/00* (2006.01)
*A61B 90/20* (2016.01)
(Continued)

(52) U.S. Cl.
CPC .......... *A61B 5/0042* (2013.01); *A61B 5/0077* (2013.01); *A61B 90/20* (2016.02);
(Continued)

(58) Field of Classification Search
CPC ...... A61B 2090/3612; A61B 2090/372; A61B 2090/373; A61B 2505/05;
(Continued)

(56) References Cited

U.S. PATENT DOCUMENTS 5,215,095 A 6/1993 Macvicar et al.
9,095,255 B2 8/2015 Fanenbruck
(Continued)

FOREIGN PATENT DOCUMENTS

DE 10 2008 040 807 A1 2/2010

OTHER PUBLICATIONS

Delschlaegel, M. et al, "Intraoperative identification of somatosensory brain areas using optical imaging and standard RGB camera equipment—a feasibility study", Current Directions in Biomedical Engineering 2015, 1:265-269.
(Continued)

*Primary Examiner* — Mark D Remaly
(74) *Attorney, Agent, or Firm* — Walter Ottesen, P.A.

(57) ABSTRACT

An apparatus is for localizing brain tissue regions connected with a brain function in a brain operating field. The apparatus includes a stimulation apparatus and a localization unit with a camera. The stimulation apparatus is configured to carry out a number of stimulation cycles. Each cycle includes a stimulation phase during which the brain function is stimulated and a rest phase during which there is no stimulation of the brain function. The localization unit records at least one stimulation image with the stimulated brain function and at least one reference image without the stimulated brain function during each stimulation cycle and uses the recorded stimulation and reference images to localize the brain tissue regions connected with the stimulated brain function. The stimulation apparatus is configured to output a feedback signal to the localization unit with at least the start of a stimulation cycle being evident from the feedback signal.

7 Claims, 3 Drawing Sheets

(51) Int. Cl.
*G16H 30/20* (2018.01)
*G16H 30/40* (2018.01)
*G16H 40/63* (2018.01)
*G16H 20/30* (2018.01)
*G16H 50/50* (2018.01)
*H04N 5/77* (2006.01)
*A61N 1/36* (2006.01)

(52) U.S. Cl.
CPC ............ *G16H 20/30* (2018.01); *G16H 30/20* (2018.01); *G16H 30/40* (2018.01); *G16H 40/63* (2018.01); *G16H 50/50* (2018.01); *A61B 2505/05* (2013.01); *A61B 2576/026* (2013.01); *A61N 1/36014* (2013.01); *H04N 5/77* (2013.01)

(58) Field of Classification Search
CPC ............ A61B 2576/026; A61B 5/0042; A61B 5/0071; A61B 5/0077; A61B 5/4064; A61B 5/4887; A61B 5/7425; A61B 90/20; A61B 90/30; A61B 90/37; A61N 1/0456; A61N 1/36014; A61N 1/36031; G16H 20/30; G16H 20/40; G16H 30/20; G16H 30/40; G16H 40/63; G16H 50/20; G16H 50/50; H04N 5/77
See application file for complete search history.

(56) References Cited

U.S. PATENT DOCUMENTS

| | | |
|---|---|---|
| 9,801,549 B2 | 10/2017 | Panitz et al. |
| 2009/0234236 A1 | 9/2009 | Lomnes et al. |
| 2010/0042000 A1 | 2/2010 | Schuhrke et al. |
| 2010/0254586 A1* | 10/2010 | Fanenbruck ......... A61B 5/0059 382/128 |
| 2017/0303844 A1 | 10/2017 | Baker et al. |
| 2020/0254260 A1* | 8/2020 | Bakker ............... A61B 5/4836 |

OTHER PUBLICATIONS

Sato, K. et al., "Intraoperative intrinsic optical imaging of human somatosensory cortex during neurosurgical operations", Neurophotonics, SPIE Digital Library, Jul.-Sep. 2017, vol. 4(3), Mar. 12, 2005, pp. 1 to 5.

Sobottka, S. et al., "Intraoperative optical imaging of intrinsic signals: a reliable method for visualizing stimulated functional brain areas during surgery", J. Neurosurg. Oct. 2013, 119:853-863.

* cited by examiner

METHOD AND APPARATUS FOR LOCALIZING BRAIN TISSUE REGIONS CONNECTED WITH A BRAIN FUNCTION

CROSS REFERENCE TO RELATED APPLICATION

This application claims priority of German patent application no. 10 2019 125 407.8, filed Sep. 20, 2019, the entire content of which is incorporated herein by reference.

FIELD OF THE INVENTION

The present disclosure relates to a method for localizing brain tissue regions connected with a brain function. Additionally, the disclosure relates to an apparatus for carrying out the method.

BACKGROUND OF THE INVENTION

When resecting brain tumors, the surgeon is presented with the challenge of removing the tumor as completely as possible and of damaging as little healthy tissue as possible in the process. In particular, regions of the brain with particular importance should be spared, for example the visual cortex which is responsible for vision or the sensory cortex which is responsible for the sense of touch.

Processes such as functional magnetic resonance imaging, for example, allow the relative position of the tumor and of functional brain tissue regions to be ascertained preoperatively. This allows the brain tissue regions to be spared to be ascertained preoperatively and allows a preparation of the resection of the brain tumor that is as sparing as possible. However, the brain tissue may shift when the skull is opened up (trepanation)—this is referred to as brain shift—which is why it is necessary to verify the relative position of the functional brain tissue regions within the exposed brain tissue. Such a verification can be implemented via intraoperative mapping of the functional brain tissue regions (so-called brain mapping). By way of example, mapping can be implemented here on the basis of measuring electrical signals on the surface of the brain tissue, the signals being triggered by peripheral stimulation at the extremities, for example.

The so-called intraoperative optical imaging (101), in which the change in the perfusion or the change in the oxygen content in the blood is ascertained upon the switch between stimulation and non-stimulation of certain brain functions, exists as a contactless alternative to mapping via electrical signals. Here, the perfusion and/or blood oxygen content can be measured by way of a change in the spectral properties of the reflection image of the brain tissue in the region of the trepanation. By way of example, methods for intraoperative optical imaging are described in M. Oelschlägel et al. "Intraoperative identification of somato-sensory brain areas using optical imaging and standard RGB camera equipment—a feasibility study", Current Directions in Biomedical Engineering 2015; 1: 265-269, in K. Sato "Intraoperative intrinsic optical imaging of human somatosensory cortex during neurosurgical operations" in Neurophotonix 4 (3), 031205 (July to September 2017), and in S. B. Sobottka "Intraoperative optical imaging of intrinsic signals: a reliable method for visualizing stimulated functional brain areas during surgery" in J. Neurosurg. 119 (2013), pages 853 to 863.

Apparatuses for intraoperative optical imaging are also integrated in surgical microscopes. By way of example, such surgical microscopes are described in US 2010/0042000 A1, U.S. Pat. No. 5,215,095 A1, U.S. Pat. No. 9,095,255 B2, U.S. Pat. No. 9,801,549 B2 and U.S. 2009/0234236 A1. Here, use is made of the fact that, as a rule, surgical microscopes include a camera for documenting the progress of the surgery in any case and that it is possible to use the camera for recording the signal for intraoperative optical imaging. Then, a so-called "activity map", that is, a map of the exposed brain tissue which indicates brain tissue regions connected with a stimulated brain function, is created on the basis of the data obtained by the intraoperative optical imaging.

For the purposes of creating the map, images of the brain operating field are recorded during a recording time period, with phases during which a certain brain function is stimulated alternating with phases without stimulation during the recording time period. In the method described in M. Oelschlägel et al. "Intraoperative identification of somatosensory brain areas using optical imaging and standard RGB camera equipment—a feasibility study", Current Directions in Biomedical Engineering 2015; 1: 265-269, the intraoperative optical imaging is implemented, for example, over a time period of 9 minutes, with 30 second stimulation phases alternating with 30 second rest phases, that is, phases without stimulation. The measurement signal finally used to create the map emerges here from the different perfusion in the brain tissue region during the stimulation and during the rest phases and/or from the different blood oxygen content during the stimulation phases and the rest phases.

Compared to the mapping via electrical signals, where electrodes are applied to the surface of the brain tissue, intraoperative optical imaging offers the advantage of not needing to touch the brain tissue during the measurement. On the other hand, it is not however simple to detect a change in the perfusion or a change in the blood oxygen content via an optical measurement (and without fluorescence) since the signals to be recorded are weak. For this reason, the measurement with the aid of intraoperative imaging is implemented over a relatively long period of time, for example the aforementioned 9 minutes with alternating 30 second stimulation phases and 30 second rest phases.

The treating surgeon is very much under time pressure during brain surgery since the intervention that is critical to the patient should be carried out as quickly as possible. At the same time, the surgeon has to carry out highly complex processes.

SUMMARY OF THE INVENTION

It is an object of the invention to provide a method and an apparatus for localizing brain tissue regions connected with a brain function, which unburden the surgeon when carrying out the method and, at the same time, facilitate a high quality of the localization of brain tissue regions connected with a brain function.

The aforementioned object can, for example, be achieved by a method for localizing brain tissue regions connected with a brain function in a brain operating field. The method includes: carrying out a number of stimulation cycles using a stimulation apparatus, wherein the stimulation cycles include a stimulation phase during which the brain function is stimulated and a rest phase during which there is no stimulation of the brain function; during the stimulation cycles, capturing via a camera at least one stimulation image with the stimulated brain function and at least one reference image without the stimulated brain function in each of the stimulation cycles using a localization unit, wherein the localization unit includes the camera; localizing the brain tissue regions connected with the stimulated brain function on a basis of the recorded stimulation and reference images; and, outputting a feedback signal to the localization unit on a basis of which a start of the stimulation cycles can be derived.

The object can, for example, also be achieved by an apparatus for localizing brain tissue regions connected with a brain function in a brain operating field. The apparatus includes: a stimulation apparatus; a localization unit having a camera; the stimulation apparatus being configured to carry out a number of stimulation cycles, wherein each stimulation cycle includes a stimulation phase during which the brain function is stimulated and a rest phase during which there is no stimulation of the brain function; the localization unit being configured to record at least one stimulation image with the stimulated brain function and at least one reference image without the stimulated brain function via the camera during each stimulation cycle and to use the recorded stimulation and reference images to localize the brain tissue regions connected with the stimulated brain function; and, the stimulation apparatus being configured to output a feedback signal to the localization unit wherein a start of the stimulation cycles is derivable from the feedback signal.

In a method for localizing in a brain operating field brain tissue regions connected with a brain function, a number of stimulation cycles are carried out using a stimulation apparatus, wherein the stimulation cycles each include a stimulation phase during which the brain function is stimulated and a rest phase during which there is no stimulation of the brain function. Here, the number of stimulation cycles contains at least one stimulation cycle but typically a plurality of stimulation cycles. At least one stimulation image with the stimulated brain function and at least one reference image without the stimulated brain function are recorded with the aid of a camera in each stimulation cycle within the scope of the stimulation cycles using a localization unit including the camera. The brain tissue regions connected with the stimulated brain function are localized on the basis of the recorded stimulation and reference images. In the method, the stimulation apparatus outputs a feedback signal to the localization unit, the start of the stimulation cycles being derivable from the feedback signal.

The feedback signal output from the stimulation apparatus to the localization unit within the scope of the method renders it possible to synchronize the recording of stimulation images and of the reference images with the stimulation cycles. This can increase the quality of the localization of the brain tissue regions connected with a brain function, leading to a sufficient localization result already being able to be obtained after, in comparison with the methods from the prior art, a shorter duration of the intraoperative optical imaging procedure, and so the time required for intraoperative optical imaging is reduced, which in turn helps shorten the surgery duration in the case of brain surgery. Additionally, the output of the feedback signal also unburdens the staff in the operating theater as it is no longer necessary to take care of the synchronization of the stimulation with the recording of the stimulation images and the reference images.

In a first configuration of the method, the localization unit and the stimulation apparatus each contain a clock. Then, the feedback signal includes a synchronization signal used to synchronize the clock of the localization unit with the clock of the stimulation apparatus and a signal indicating the duration of the stimulation cycles and the start time of the first stimulation cycle. On the basis of the feedback signal, the localization unit is then able to ascertain the exact start and end times of each stimulation cycle from the start time and the duration of the stimulation cycles. In this way, recorded images can be precisely assigned to a stimulation phase or a rest phase. By way of example, the images could be provided with timestamps, with the aid of which the localization unit can assign the images to a certain stimulation phase or a certain rest phase, the temporal arrangement of which is known to the localization unit on account of the feedback signal. Since an incorrect assignment would reduce the quality of the localization of brain tissue regions connected with brain function, the feedback signal can ensure a high quality of this localization. If necessary, the synchronization of the clocks can be repeated after certain time intervals by a renewed transmission of a synchronization signal from the stimulation apparatus to the localization unit in order to compensate for a possible drift.

In this configuration of the method, the feedback signal could also specify the number of stimulation cycles such that the time of the end of the measuring process can also be ascertained. Alternatively, the stimulation apparatus can also output a signal indicating the end of the stimulation cycles to the localization unit. Should the duration of the stimulation phases and of the rest phases vary within the stimulation cycles, the feedback signal can moreover contain a signal which reveals the transition times between stimulation phases and rest phases.

In a second configuration of the method, the feedback signal contains start signals and stop signals, wherein each start signal indicates the start of a stimulation phase and each stop signal indicates the end of a stimulation phase. Since rest phases are present between the stimulation phases, the start and end of rest phases also emerges from the start and stop signals. Alternatively, each start signal can also indicate the start of a rest phase and each stop signal can indicate the end of a rest phase. Since stimulation phases are present between the rest phases, the start and end of stimulation phases also emerges from the start and stop signals. In the second configuration of the method, too, the recorded images can be precisely assigned to a stimulation phase or a rest phase. Here, there is no need to synchronize clocks, and so use can also be made of stimulation apparatuses and/or localization units without clocks. Moreover, the string of the feedback signal is simpler than in the first configuration. Since the stimulation cycles contain no further phases apart from the stimulation phases and the rest phases, the start of a new stimulation cycle also emerges from the start and stop signals.

In an embodiment of the method, the localization unit can examine the at least one stimulation image and the at least one reference image for interferences following the end of a stimulation cycle. To avoid poor data having a negative influence on the localization, the at least one examined stimulation image and the at least one examined reference image are not used for localizing the brain tissue regions connected with the stimulated brain function if the examination yields that the interferences exceed a predetermined measure. The stimulation cycles and the recording of stimulation images and reference images can be continued while the at least one stimulation image and the at least one reference image are examined for interferences so as to avoid interruptions in the localization process. If the intention is for a reduction in the number of stimulation cycles that are usable for the localization to be avoided, an additional stimulation cycle can be carried out for each stimulation cycle for which the examination yields that the interferences exceed the predetermined measure. The additional stimulation cycle can be carried out after the end of the last regular stimulation cycle.

According to a second aspect of the disclosure, an apparatus for localizing in a brain operating field brain tissue regions connected with a brain function is made available. The apparatus includes a stimulation apparatus and a localization unit with a camera. The stimulation apparatus is configured to carry out a number of stimulation cycles, wherein each stimulation cycle includes a stimulation phase during which the brain function is stimulated and a rest phase during which there is no stimulation of the brain function. Here, the number of stimulation cycles contains at least one stimulation cycle but typically a plurality of stimulation cycles. The localization unit is configured to record at least one stimulation image with the stimulated brain function and at least one reference image without the stimulated brain function with the aid of the camera during each stimulation cycle and to use the recorded stimulation and reference images to localize the brain tissue regions connected with the stimulated brain function. The stimulation apparatus is moreover configured to output a feedback signal to the localization unit, the start of the stimulation cycles being derivable from the feedback signal.

The feedback signal output from the stimulation apparatus to the localization unit facilitates synchronization of the recording of the stimulation images and the reference images with the stimulation cycles, allowing the method to be carried out. Consequently, the apparatus also facilitates the realization of the properties described with reference to the method and allows the advantages described with reference to the method according to the disclosure to be achieved. Therefore, reference in this respect is made to the description of the method according to the disclosure and the embodiments thereof.

In a first configuration of the apparatus, the localization unit and the stimulation apparatus each contain a clock. Then, the feedback signal includes a synchronization signal used to synchronize the clock of the localization unit with the clock of the stimulation apparatus and a signal indicating the duration of the stimulation cycles and the start time of the first stimulation cycle. Moreover, the feedback signal can specify the number of stimulation cycles. Alternatively, the stimulation apparatus can also be configured to output a signal indicating the end of the stimulation cycles to the localization unit. Should the duration of the stimulation phases and of the rest phases vary within the stimulation cycles, the feedback signal can moreover contain a signal which reveals the transition times between stimulation phases and rest phases.

In a second configuration of the apparatus, the feedback signal contains start signals and stop signals, wherein each start signal indicates the start of a stimulation phase and each stop signal indicates the end of a stimulation phase or each start signal indicates the start of a rest phase and each stop signal indicates the end of a rest phase.

In an embodiment of the apparatus, the localization unit can be configured to examine the at least one stimulation image and the at least one reference image for interferences following the end of the stimulation cycle and not to use the at least one stimulation image and the at least one reference image of the stimulation cycle for localizing the brain tissue regions connected with the stimulated brain function if the examination yields that the interferences exceed a predetermined measure. Moreover, the localization unit and the stimulation apparatus can be configured to continue the stimulation cycles and the recording of stimulation images and reference images while the at least one stimulation image and the at least one reference image are examined for interferences. For each stimulation cycle for which the examination yields that the interferences exceed the predetermined measure the localization unit is able to prompt the stimulation apparatus to carry out an additional stimulation cycle.

Within the scope of the present disclosure, the localization unit can be integrated in a surgical microscope.

The described embodiments of the apparatus allow the above-described embodiments of the method to be carried out. The properties and advantages described with reference to the embodiments of the method can therefore be realized with the described embodiments of the apparatus.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
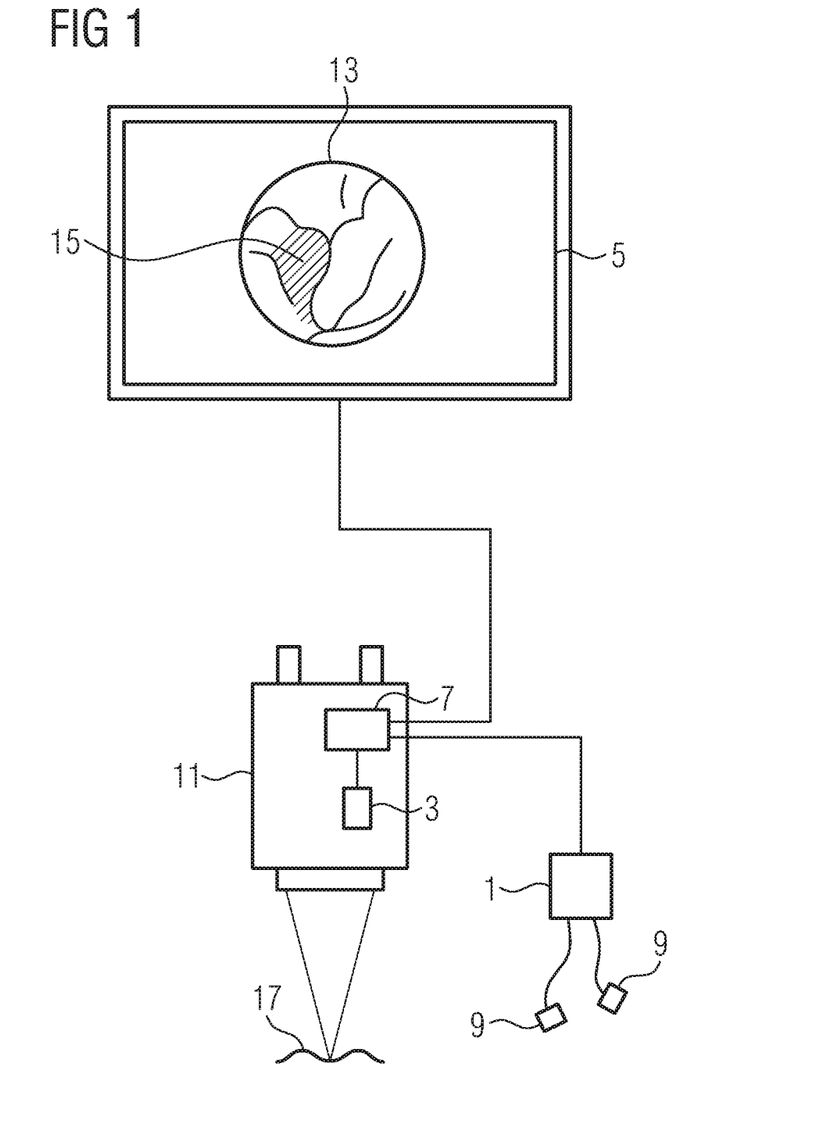
FIG. 1 shows an apparatus for localizing brain tissue regions connected with a brain function.
Figure 2:
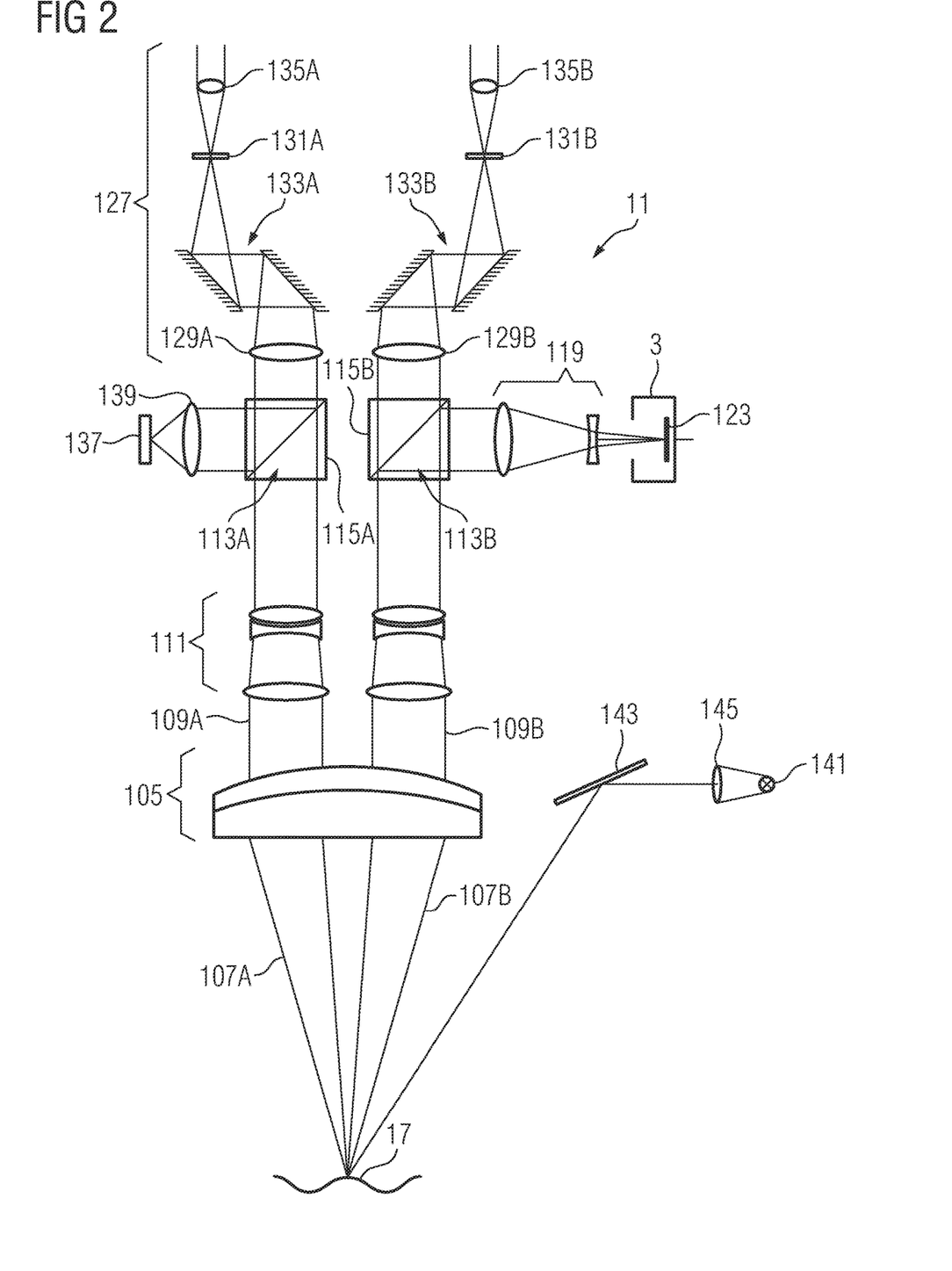
FIG. 2 shows the structure of a surgical microscope in a schematic illustration; and, FIG. 3 shows an alternative embodiment of the surgical microscope.
Figure 3:
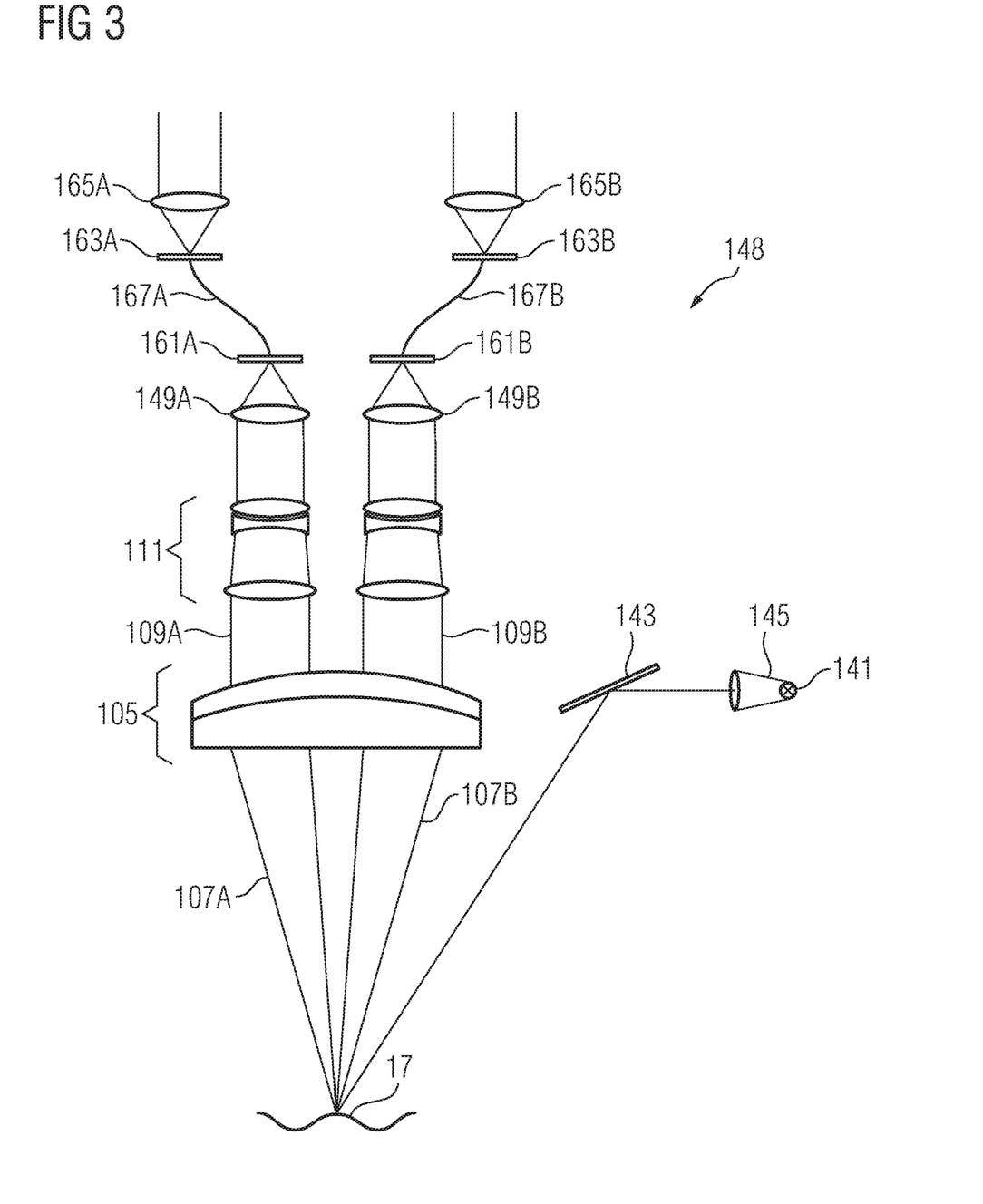

Exemplary embodiments are described below on the basis of FIGS. 1 to 3. Here, FIG. 1 shows an embodiment of an apparatus for localizing brain tissue regions connected with a brain function. FIGS. 2 and 3 show examples of the structure of surgical microscopes, as may find use within the scope of the apparatus shown in FIG. 1.

In the embodiment of the apparatus for localizing brain tissue regions connected with a brain function, as shown in FIG. 1, the apparatus includes a stimulation apparatus in the form of a nerve stimulator 1, a camera 3, a display apparatus in the form of a monitor 5 and an evaluation apparatus 7, which is connected to the nerve stimulator 1, the camera 3 and the monitor 5 for signal transmission purposes. In the present embodiment, the evaluation apparatus 7 forms a localization unit together with the camera 3, the localization unit, on the basis of stimulation cycles performed by the nerve stimulator 1, localizing in the brain operating field 17 the brain tissue regions connected with the respectively stimulated brain function or respectively stimulated brain functions. A plurality of such stimulation cycles are carried out in the present embodiment.

In the present embodiment, the nerve stimulator 1 is embodied for the electrical stimulation of nerves. To this end, it includes a number of electrodes 9, with the aid of which nerves of the peripheral nervous system, such as the median nerve, which is responsible for motor control of the forearm muscles and some finger muscles and for the sensitive innervation of the palm of the hand and the thumb up to the inner side of the ring finger, or the trigeminal nerve, which is responsible for sensitive perception in the face and for the motor system of the face, oral cavity, and muscles of mastication, can be electrically stimulated.

The camera 3 is part of a surgical microscope 11 in the present embodiment. As a rule, surgical microscopes contain a camera for documentation purposes, it being possible to use the camera for recording stimulation images and reference images during an intraoperative optical imaging process. The camera 3 includes an electronic image sensor and is controlled by the evaluation apparatus 7. Moreover, digital images recorded by an electronic camera chip of the camera 3 are output to the evaluation apparatus 7.

In FIG. 1, the evaluation apparatus 7 is presented as integrated in the surgical microscope 11. However, it is evident to a person skilled in the art that the evaluation apparatus 7 need not necessarily be integrated in the surgical microscope 11. In particular, the evaluation apparatus 7 can also be configured as a unit that is independent of the surgical microscope 11. The same applies to the camera 3 of the localization unit. Should the evaluation apparatus 7 be an independent unit, it may be formed by a commercially available PC, for example, on which a suitable computer program runs.

Apart from controlling the camera 3, the evaluation apparatus 7 is also responsible for localizing on the basis of stimulation images and reference images recorded with the aid of the camera 3 and in the brain operating field 17 the brain tissue regions connected with the respectively stimulated brain function or the respectively stimulated brain functions. Then, by way of the evaluation apparatus 7, the localized brain tissue regions can be presented on the monitor 5 in the form of a map of the brain operating field 17, in which map the brain tissue regions 15 connected with the respectively stimulated brain function or the respectively stimulated brain functions are marked. FIG. 1 shows, very schematically, a map 13 presented on the monitor 5, a brain tissue region 15 connected with a stimulated brain function being marked in the map. The marking, illustrated by hatching in FIG. 1, can be implemented, for example, by coloring the brain tissue region connected with the stimulated brain function, by edging the brain tissue region connected with the stimulated brain function, by reducing the color saturation of brain tissue regions situated outside of the brain tissue region connected with the stimulated brain function, et cetera. Should the map 13 be intended to mark out different brain tissue regions connected with different stimulated brain functions, then this can be implemented by different coloring, for example. In principle, instead of distinguishing brain tissue regions assigned to different brain functions by way of color, the different brain tissue regions could be labeled in distinguishable fashion in any other way, for example by coloring a brain tissue region connected with a first brain function and edging a second brain tissue region connected with a second brain function. If it is not the distinction between different brain functions that is important but only whether a certain brain tissue region is connected with one of the stimulated brain functions, this marking can also be implemented in the same color. In principle, any representation suitable for distinguishing the brain tissue regions 15 connected with the stimulated brain functions from those not connected with the stimulated brain functions is possible within the scope of the present disclosure. Further elements could be presented on the monitor 5 next to the current map 13, for instance quality parameters assigned to maps or the like.

During a stimulation cycle carried out within the scope of an intraoperative optical imaging process there is in succession a phase of stimulating a certain brain function with the aid of the nerve stimulator 1, referred to as stimulation phase, and a phase without stimulation of the brain function, referred to as rest phase. In the process, the evaluation apparatus 7 controls the camera 3 in such a way that at least one stimulation image of the brain operating field 17, that is, an image containing an optical signal caused by the stimulation, and at least one reference image, that is, an image which contains no optical signal caused by the stimulation, are recorded during a stimulation cycle. In the present embodiment, at least one video sequence of the brain operating field 17 is recorded by the camera 3 during an intraoperative optical imaging process. Then, the stimulation images and reference images are frames of the video sequence.

A number of stimulation cycles are strung together within the scope of the intraoperative optical imaging process such that rest phases and stimulation phases alternate over a certain period of time. By way of example, use can be made of stimulation cycles as described in M. Oelschlägel et al. "Intraoperative identification of somato-sensory brain areas using optical imaging and standard RGB camera equipment—a feasibility study", Current Directions in Biomedical Engineering 2015; 1: 265-269, that is, 30 second stimulation phases and 30 second rest phases alternating over 9 minutes. In the present embodiment, the intraoperative optical imaging process includes a total of 9 stimulation phases and 9 rest phases, which can finally be used to create the map 13. However, the intraoperative optical imaging process could also include more than or fewer than 9 stimulation cycles. Moreover, the duration of the stimulation phases and the rest phases could be longer or shorter than 30 seconds. Also, the duration of a stimulation phase need not correspond to the duration of a rest phase.

The intraoperative imaging process is started by the user by way of an input in the evaluation apparatus 7, which then initiates the stimulation cycles being carried out by the nerve stimulator 1. Following the initiation of the stimulation cycles, the nerve stimulator 1 generates a feedback signal which it outputs to the evaluation apparatus 7. In an embodiment, the evaluation apparatus 7 and the nerve stimulator 1 each contain a clock and the feedback signal includes a synchronization signal used to synchronize the clock of the evaluation apparatus 7 with the clock of the stimulation apparatus 1. Moreover, the feedback signal of the present embodiment includes a signal indicating the duration of the stimulation cycles, the start time of the first stimulation cycle, and the number of stimulation cycles. On the basis of the information contained in the feedback signal, the evaluation apparatus 7 ascertains the start points of the respective stimulation cycles and synchronizes the image recording and the evaluation with the stimulation cycle carried out by the nerve stimulator 1. Here, each frame of the video recording the brain operating field 17 can receive a timestamp, for example, on the basis of which the frame can be unambiguously assigned to a time within the stimulation cycle. Since the duration of the stimulation phases and the rest phases is known and constant in the present embodiment, this allows precise ascertainment of the stimulation phase or rest phase to which any given frame should be assigned and precise ascertainment of the temporal relationship between the frame and this stimulation phase or rest phase, that is, whether the frame was recorded at the start, at the end or in the middle of the corresponding phase. Moreover, the synchronization allows a precise statement as regards to the frames at which a change from a stimulation phase to a rest phase, or vice versa, has occurred. The exact assignment of the frames to the times in the stimulation cycle, facilitated by the synchronization, can increase the quality of the evaluation of the stimulation images and of the reference images, for example because it is possible to avoid incorrect assignments of individual frames to a stimulation phase rather than a rest phase, or vice versa.

In an alternative embodiment, the feedback signal contains start and stop signals, which are respectively emitted when a stimulation phase starts or ends, instead of the synchronization signal and the signal specifying the duration of the stimulation cycles, the start time of the first stimulation cycle, and the number of stimulation cycles. When the evaluation apparatus 7 receives a start signal or stop signal from the nerve stimulator 1, the frame recorded by the camera 3 at the corresponding time is marked accordingly. Here, the evaluation apparatus 7 can also contain a counter that is incremented by one with each reception of a start signal such that information relating to the ordinal position of the started or ended stimulation phase can also be added to the respectively marked frames. The presence of a clock in the nerve stimulator 1 and in the evaluation apparatus 7 or the synchronization of clocks possibly present is not required in this embodiment. Even though the start and stop signals of the described embodiment each mark the start and the end of a stimulation phase they could also mark the start and the end of a rest phase.

Independently of the type of feedback signal, the evaluation apparatus 7 examines the recorded frames for interferences. If interferences that exceed a predetermined measure are determined, the evaluation apparatus 7 does not use the frames of this stimulation cycle for localizing the brain tissue regions 15 connected with the stimulated brain function. Interferences that could render the frames unusable for the purposes of localizing the brain tissue regions 15 connected with the stimulation could include illumination reflections, bleeding or the like. The stimulation cycles are not halted during the evaluation, and so the sequence of stimulation phases and rest phases is continued without interruption.

In the present embodiment, an additional stimulation cycle is appended for each stimulation cycle whose frames are not used to localize the brain tissue regions 15 connected with the stimulated brain function, and so the specified number of stimulation cycles can be used to localize the brain tissue regions 15 connected with the stimulated brain function. Here, it is possible to limit the number of possible appended stimulation cycles to prevent a maximum duration of the intraoperative imaging from being exceeded. If necessary, the localization of the brain tissue regions 15 connected with the stimulated brain function can be based on a reduced number of stimulation cycles or the method can be terminated prematurely should there be interferences in too many stimulation cycles. Following termination of the method, parameters such as the illumination or the orientation of the surgical microscope 11 in relation to the brain operating field 17 could be altered and the method could be restarted after these parameters have been altered. Such a restart can be implemented automatically within the scope of the present disclosure by virtue of the evaluation apparatus 7 outputting a restart command to the nerve stimulator 1, which thereupon restarts the method and outputs a feedback signal to the evaluation apparatus 7.

Provided enough interference-free stimulation cycles are present, the frames are evaluated in view of the localization of the brain tissue regions 15 connected with the stimulated brain function and the corresponding brain tissue regions 15 are displayed on the monitor 5 in the form of a map 13. In principle, the evaluation can be implemented here with any suitable process, for example the process described in S. B. Sobottka et al. "Intraoperative optical imaging of intrinsic signals: a reliable method for visualizing stimulated functional brain areas during surgery", J. Neurosurg 119 (2013), pages 853-863 or the process described in U.S. Pat. No. 9,095,255 B2.

FIG. 2 shows a schematic illustration of a possible structure of the surgical microscope 11, as can find use in the apparatus of FIG. 1. FIG. 3 shows a possible alternative structure.

The surgical microscope 11 shown in FIG. 2 includes, as essential components, an objective 105 that should face an object field 17, the brain operating field 17 in the present embodiment, the objective, in particular, being able to be embodied as an achromatic or apochromatic objective. In the present embodiment, the objective 105 has two partial lenses that are cemented to one another and form an achromatic objective. The object field 17 is arranged in the focal plane of the objective 105 such that it is imaged at infinity by the objective 105. Expressed differently, a divergent beam 107A, 107B emanating from the object field 17 is converted into a parallel beam 109A, 109B during its passage through the objective 105.

A magnification changer 111 is arranged on the observer side of the objective 105, which magnification changer can be embodied either as a zoom system for changing the magnification factor in a continuously variable manner as in the illustrated embodiment, or as what is known as a Galilean changer for changing the magnification factor in a stepwise manner. In a zoom system, constructed by way of example from a lens combination having three lenses, the two object-side lenses can be displaced in order to vary the magnification factor. In actual fact, however, the zoom system also can have more than three lenses, for example four or more lenses, in which case the outer lenses then can also be arranged in a fixed manner. In a Galilean changer, by contrast, there are a plurality of fixed lens combinations which represent different magnification factors and which can be introduced into the beam path alternately. Both a zoom system and a Galilean changer convert an object-side parallel beam into an observer-side parallel beam having a different beam diameter. In the present embodiment, the magnification changer 111 already is part of the binocular beam path of the surgical microscope 11, that is, it has a dedicated lens combination for each stereoscopic partial beam path 109A, 109B of the surgical microscope 11. In the present embodiment, a magnification factor is adjusted via the magnification changer 111 by way of a motor-driven actuator which, together with the magnification changer 111, is part of a magnification changing unit for adjusting the magnification factor.

The magnification changer 111 is adjoined on the observer side by an interface arrangement 113A, 113B, via which external devices can be connected to the surgical microscope 11 and which includes beam splitter prisms 115A, 115B in the present embodiment. However, in principle, use can also be made of other types of beam splitters, for example partly transmissive mirrors. In the present embodiment, the interfaces 113A, 113B serve to output couple a beam from the beam path of the surgical microscope 11 (beam splitter prism 115B) and to input couple a beam into the beam path of the surgical microscope 11 (beam splitter prism 115A).

In the present embodiment, the beam splitter prism 115A in the partial beam path 109A serves to mirror information or data for an observer into the partial beam path 109A of the surgical microscope 11 with the aid of a display 37, for example a digital mirror device (DMD) or an LCD display, and an associated optical unit 139 via the beam splitter prism 115A. In the case of brain surgery, it is possible, for example, to mirror-in the map 13 of the brain operating field 17, in which brain tissue regions 15 connected with at least one stimulated brain function are marked. A camera adapter 119 with a camera 3 fastened thereto, the camera being equipped with an electronic image sensor 123, for example with a CCD sensor or a CMOS sensor, is arranged at the interface 113B in the other partial beam path 109B. It is possible via the camera 3 to record an electronic image and, in particular, a digital image of the object field 17. In particular, a hyperspectral sensor also can find use as an image sensor, the hyperspectral sensor having not only three spectral channels (for example, red, green and blue) but also a multiplicity of spectral channels. In the embodiment shown in FIG. 1, the camera 3 is used to record video sequences containing the stimulation images and reference images.

The interface 113 is adjoined on the observer side by a binocular tube 127. The latter has two tube objectives 129A, 129B, which focus the respective parallel beam 109A, 109B onto an intermediate image plane 131, that is, image the object field 17 onto the respective intermediate image plane 131A, 131B.

The intermediate images situated in the intermediate image planes 131A, 131B are finally imaged at infinity in turn by eyepiece lenses 135A, 135B, such that an observer can observe the intermediate image with a relaxed eye. Moreover, an increase in the distance between the two partial beams 109A, 109B is implemented in the binocular tube via a mirror system or via prisms 133A, 133B in order to adapt the distance to the interocular distance of the observer. In addition, image erection is carried out by the mirror system or the prisms 133A, 133B.

The surgical microscope 11 moreover is equipped with an illumination apparatus, via which the object field 17 can be illuminated with broadband illumination light. To this end, the illumination apparatus has a white-light source 141, for example a halogen lamp or a gas discharge lamp, in the present embodiment. The light emanating from the white-light source 141 is directed in the direction of the object field 17 via a deflection mirror 143 or a deflection prism in order to illuminate the field. Furthermore, an illumination optical unit 145 is present in the illumination apparatus, the illumination optical unit ensuring uniform illumination of the entire observed object field 17.

Reference is made to the fact that the illumination beam path illustrated in FIG. 2 is very schematic and does not necessarily reproduce the actual course of the illumination beam path. In principle, the illumination beam path can be embodied as so-called oblique illumination, which comes closest to the schematic illustration in FIG. 2. In such oblique illumination, the beam path extends at a relatively large angle (6° or more) with respect to the optical axis of the objective 105 and, as illustrated in FIG. 2, may extend completely outside the objective. Alternatively, however, there is also the possibility of allowing the illumination beam path of the oblique illumination to extend through a marginal region of the objective 105. A further option for arranging the illumination beam path is what is known as 0° illumination, in which the illumination beam path extends through the objective 105 and is coupled into the objective 105 between the two partial beam paths 109A, 109B, along the optical axis of the objective 105 in the direction of the object field 17. Finally, it is also possible to embody the illumination beam path as so-called coaxial illumination, in which a first illumination partial beam path and a second illumination partial beam path are present. The partial beam paths are input coupled into the surgical microscope 11 in a manner parallel to the optical axes of the observation partial beam paths 109A, 109B by way of one or more beam splitters such that the illumination extends coaxially in relation to the two observation partial beam paths.

The illumination can be influenced in the surgical microscope 11 illustrated in FIG. 2. By way of example, a filter can be introduced into the illumination beam path, the former only passing a narrow spectral range of the broad spectrum of the white light source 141, for example a spectral range that can be used to excite fluorescence of a fluorescent dye situated in the object field 17. In order to observe the fluorescence, filters 137A, 137B can be introduced into the observation partial beam paths, the filters filtering out the spectral range used to excite the fluorescence so that the fluorescence can be observed. Within the scope of the present embodiment, a filter can be introduced into the illumination beam path when recording the stimulation images and the reference images, the filter only passing those wavelength ranges of the illumination light in which a change in the perfusion or a change in the blood oxygen content generates a particularly clear signal in the observation beam path.

In the embodiment variant of the surgical microscope 11 shown in FIG. 2, the objective 105 consists only of an achromatic lens. However, use can also be made of an objective lens system made of a plurality of lenses, in particular a so-called vario-objective, via which it is possible to vary the working distance of the surgical microscope 11, that is, the distance between the object-side focal plane and the vertex of the first object-side lens surface of the objective 105, also referred to as front focal distance. The object field 17 arranged in the focal plane is imaged at infinity by a vario-objective 50, too, and so a parallel beam is present on the observer side.

FIG. 3 shows a schematic illustration of an example of a digital surgical microscope 148. In this surgical microscope, the main objective 105, the magnification changer 111 and the illumination system 141, 143, 145 do not differ from the surgical microscope 2 with the optical view that is illustrated in FIG. 2. The difference lies in the fact that the surgical microscope 148 shown in FIG. 3 does not include an optical binocular tube. Instead of the tube objectives 129A, 129B from FIG. 2, the surgical microscope 148 from FIG. 3 includes focusing lenses 149A, 149B, via which the binocular observation beam paths 109A, 109B are imaged on digital image sensors 161A, 161B. Here, the digital image sensors 161A, 161B can be, for example, CCD sensors or CMOS sensors. The images recorded by the image sensors 161A, 161B are transmitted digitally to digital displays 163A, 163B, which may be embodied as LED displays, as LCD displays or as displays based on organic light-emitting diodes (OLEDs). Like in the present example, eyepiece lenses 165A, 165B can be assigned to the displays 163A, 163B, via which the images displayed on the displays 163A, 163B are imaged at infinity such that an observer can observe the images with relaxed eyes. The displays 163A, 163B and the eyepiece lenses 165A, 165B can be part of a digital binocular tube; however, they can also be part of a head-mounted display (HMD) such as, for example, a pair of smartglasses.

In the embodiment shown in FIG. 1, the video sequences containing the stimulation images and the reference images can be recorded by at least one of the digital image sensors 161A, 161B. In this case, the digital image sensor or the digital image sensors represent the imaging apparatus from FIG. 1.

Even though FIG. 3, like FIG. 2, only illustrates an achromatic lens 105 with a fixed focal length, the surgical microscope 148 shown in FIG. 3 may include a varioscope objective instead of the objective lens 105, like the surgical microscope 11 illustrated in FIG. 2. Furthermore, FIG. 3 shows a transfer of the images recorded by the image sensors 161A, 161B to the displays 163A, 163B via cables 167A, 167B. Instead of in wired fashion, the images could also be transmitted wirelessly to the displays 163A, 163B, particularly if the displays 163A, 163B are part of a head-mounted display.

The present invention has been described in detail on the basis of embodiments for purposes of explanation. However, it is evident to a person skilled in the art that it is possible within the scope of the invention to deviate from the specific embodiments, as has already been mentioned within the scope of the description of the embodiments. The scope of protection of the invention should therefore not be restricted by the embodiments but only by the attached claims.

LIST OF REFERENCE NUMERALS

1 Nerve stimulator
3 Camera
5 Monitor
7 Evaluation apparatus
9 Electrode
11 Surgical microscope
13 Map
15 Brain tissue region connected with a stimulated brain function
17 Brain operating field
50 Vario-objective
105 Objective
107 A,B Divergent beam
109 A,B Parallel beam
111 Magnification changer
113 A,B Interface arrangement
115 A,B Beam splitter prism
119 Camera adapter
123 Image sensor
127 Binocular tube
129 A,B Tube objective
131 A,B Intermediate image plane
133 A,B Prism
135 A,B Eyepiece lens
137 Display
137A, B Filters
139 Optical unit
141 White light source
143 Deflection mirror
145 Illumination optical unit
148 Surgical microscope
149 A,B Focusing lens
161 A,B Image sensor
163 A,B Display
165 A,B Eyepiece lens
167 A,B Cable

What is claimed is:

1. A method for localizing brain tissue regions connected with a brain function in a brain operating field, the method comprising:

carrying out a number of stimulation cycles using a stimulation apparatus, wherein the stimulation cycles each include a stimulation phase during which the brain function is stimulated and a rest phase during which there is no stimulation of the brain function;

during the stimulation cycles, recording via a camera at least one stimulation image frame with the stimulated brain function and at least one reference image frame without the stimulated brain function in each of the stimulation cycles using a localization unit, wherein the localization unit includes the camera;

localizing the brain tissue regions connected with the stimulated brain function on a basis of the recorded stimulation and reference images;

outputting a feedback signal from the stimulation apparatus to the localization unit on a basis of which a start of the stimulation cycles can be derived;

wherein the feedback signal includes start signals and stop signals, wherein each start signal indicates a start of a stimulation phase and each stop signal indicates an end of a stimulation phase or each start signal indicates a start of a rest phase and each stop signal indicates an end of a rest phase; and, assigning recorded images to a stimulation phase or a rest phase based on said start or stop signal.

2. The method of claim 1, wherein the localization unit and the stimulation apparatus each have a clock; and, the feedback signal includes a synchronization signal used to synchronize the clock of the localization unit with the clock of the stimulation apparatus and a signal indicating a duration of the stimulation cycles and a start time of a first stimulation cycle.

3. The method of claim 2, wherein the number of stimulation cycles is specified in the feedback signal.

4. The method of claim 1 further comprising examining the at least one stimulation image and the at least one reference image for interferences following an end of a stimulation cycle and not using the at least one examined stimulation image and the at least one examined reference image for said localizing the brain tissue regions connected with the stimulated brain function on a basis of the recorded stimulation and reference images if said examining yields that the interferences exceed a predetermined measure.

5. The method of claim 4, wherein the stimulation cycles and the recording of stimulation images and reference images is continued while the at least one stimulation image and the at least one reference image are examined for interferences.

6. The method of claim 4, wherein an additional stimulation cycle is carried out for each stimulation cycle for which the examination yields that the interferences exceed the predetermined measure.

7. The method of claim 1, wherein the method comprises the step of processing the feedback signal to synchronize the recording of stimulation images and of the reference images with the stimulation cycle.

* * * * *

UNITED STATES PATENT AND TRADEMARK OFFICE
CERTIFICATE OF CORRECTION

| | |
|---|---|
| PATENT NO. | : 11,744,466 B2 |
| APPLICATION NO. | : 17/025905 |
| DATED | : September 5, 2023 |
| INVENTOR(S) | : Christoph Hauger et al. |

It is certified that error appears in the above-identified patent and that said Letters Patent is hereby corrected as shown below:

On the Title Page

Under OTHER PUBLICATIONS: delete "Delschlaegel" and substitute -- Oelschlaegel -- therefor.

In the Specification

In Column 1:
Line 45: delete "(101)" and substitute -- (IOI) -- therefor.

Signed and Sealed this
Ninth Day of January, 2024

*Katherine Kelly Vidal*

Katherine Kelly Vidal
*Director of the United States Patent and Trademark Office*